United States Patent
Dijkstra

(10) Patent No.: US 8,563,807 B2
(45) Date of Patent: Oct. 22, 2013

(54) HYBRID SPINACH VARIETY ANDROMEDA

(75) Inventor: Jan Dijkstra, Beegden (NL)

(73) Assignee: Nunhems B.V., Nunhem (NL)

( * ) Notice: Subject to any disclaimer, the term of this patent is extended or adjusted under 35 U.S.C. 154(b) by 121 days.

(21) Appl. No.: 13/034,821

(22) Filed: Feb. 25, 2011

(65) Prior Publication Data

US 2012/0222147 A1    Aug. 30, 2012

(51) Int. Cl.
- *A01H 1/00* (2006.01)
- *C07H 21/04* (2006.01)
- *C07K 14/415* (2006.01)
- *C12N 15/00* (2006.01)

(52) U.S. Cl.
USPC ........... 800/295; 435/412; 435/418; 435/468; 536/23.1; 800/260; 800/278

(58) Field of Classification Search
USPC ........................................... 800/295
See application file for complete search history.

(56) References Cited

U.S. PATENT DOCUMENTS 7,935,867 B2 *   5/2011   Baerends ...................... 800/295

* cited by examiner

*Primary Examiner* — Li Zheng

(57) ABSTRACT

The invention provides a new and distinct hybrid variety of spinach, NUN 0002 SP or Andromeda F1, which is characterized by producing high quality leaves for the fresh market and/or the processing industry.

20 Claims, No Drawings

HYBRID SPINACH VARIETY ANDROMEDA

CROSS-REFERENCE TO RELATED APPLICATIONS

This application claims priority under 35 U.S.C. 119(a)-(d) to CPVO Application No. 2011/0120, filed by Nunhems B. V. on 17 Jan. 2011, the disclosure of which is herein incorporated by reference in its entirety.

FIELD OF THE INVENTION

The present invention relates to the field of plant breeding. In particular, the invention provides for a new and distinct hybrid variety of spinach (*Spinacia oleracea*) designated NUN 0002 SP (or "Andromeda" or "Andromeda F1"). The invention provides seeds, plants and plant parts (e.g. leaves, fruits, gametes, flowers, etc.), as well as tissue and/or cell cultures of Andromeda and methods for producing a spinach plant by crossing Andromeda with itself or with another spinach plant, such as another spinach variety, line, landrace or wild accession (e.g. *S. turkestanica, S. tetranda*).

The new variety is resistant to downy mildew (*Peronospora farinose* f.sp. *spinaciae*, abbreviated as Pf) races Pf 1-11 and UA2209. The most similar varieties Lazio and Whale do not have the same Pf resistances, as Lazio has Pf 1-10 resistance (lacking Pf 11 and UA 2209 resistance) and Whale has Pf 1-9 and Pf 11 resistance (lacking Pf 10 and UA2209 resistance). Andromeda is also earlier than Lazio and Whale. Further morphological and physiological differences between Andromeda and Lazio are seen in plant habit (semi-erect in Andromeda vs. flat in Lazio), leaf margin of the first foliage leaves (flat vs. slightly curled), leaf tip (round-pointed vs. round) and blade lobing (lobed vs. not lobed) of prime market stage leaves and petiole pigmentation (absent vs. present) and petiole length (medium vs. short). Also blade size of prime market stage leaves is slightly larger in Andromeda compared to Lazio. Andromeda is, thus, distinct from varieties Lazio and Whale in a number of genetically determined characteristics, as can be compared when grown under the same environmental conditions. See also Tables 1, 2 and 3 herein.

Provided are seeds of Andromeda, plants and plant parts produced from these seeds (such as leaves), vegetative reproductions of the variety Andromeda, and progeny of the variety. Thus also provided are spinach plants (and seeds from which such plants can be grown) having all the morphological and physiological characteristics of Andromeda.

SUMMARY OF THE INVENTION

The invention provides for a new hybrid variety of spinach called NUN 0002 SP (also designated as Andromeda). The invention also provides for a plurality of seeds of the new variety, containers comprising a plurality of seeds, plants produced from growing the seeds and plant parts obtainable from the grown plant, such as (harvested) leaves.

Thus, in one aspect, the invention provides for seeds of spinach variety designated NUN 0002 SP, wherein a representative sample of seeds of said variety is to be deposited under Accession Number NCIMB 42156.

In another aspect, the invention provides for a plant or plant part of spinach variety NUN 0002 SP, a representative sample of seed from said variety is to be deposited under Accession Number NCIMB 42156.

In other aspects, the invention provides for plant parts, such as pollen, flowers, leaves, cuttings, embryos, cotyledons, petioles, anthers, roots, root tips, shoots, stalks, seeds, pistils, etc. of variety NUN 0002 SP, or parts of any of these.

In other aspects, the invention provides for progeny of variety NUN 0002 SP such as progeny obtained by selfing NUN 0002 SP one or more times and/or cross-pollinating NUN 0002 SP with another spinach plant or variety one or more times. In particular, the invention provides for progeny that retain all the morphological and physiological characteristics of NUN 0002 SP when grown under the same environmental conditions. In one embodiment the progeny exhibit a combination of 2, 3, 4, 5 or more traits selected from those of Table 2 and/or 3, in particular from the group consisting of: arrow shaped leaves, medium green upper leaf color, dull leaf luster, medium-to-late start of bolting (earliness), spineless seeds (smooth seed surface), semi-erect plant habit, resistance to downy mildew races Pf 1-11 and race UA2209, wherein the combination of traits is controlled by genetic means found in spinach variety NUN 0002 SP.

In one aspect a spinach plant is provided, and a seed from which the plant can be grown, that exhibits a combination of 2, 3, 4, 5 or more traits selected from those of Table 2 and/or 3, in particular from the group consisting of: arrow shaped leaves, medium green upper leaf color, dull leaf luster, medium-to-late start of bolting (earliness), spineless seeds (smooth seed surface), semi-erect plant habit, resistance to downy mildew races Pf 1-11 and race UA2209, wherein the combination of traits is controlled by genetic means found in spinach variety NUN 0002 SP.

In another aspect, the invention provides for vegetative reproductions of the variety NUN 0002 SP and for essentially derived varieties (EDVs) of NUN 0002 SP. Vegetative reproductions of the variety in one aspect of the invention retain all the morphological and physiological characteristics of NUN 0002 SP when grown under the same environmental conditions. EDVs of NUN 0002 SP in one aspect retain essentially all the morphological and physiological characteristics of NUN 0002 SP (the initial variety), but may differ to some degree from the initial variety.

DEFINITIONS

"Spinach" refers herein to plants of the species *Spinacia oleracea* L.

"UPOV descriptors" are the plant variety descriptors described for spinach in the "Guidelines for the Conduct of Tests for Distinctness, Uniformity and Stability," TG/55/7 (Geneva 2007), as published by UPOV (International Union for the Protection of New Varieties and Plants, available on the world wide web at upov.int) and which can be downloaded from the world wide web at upov.int/en/publications/tg_rom/tg_index.html, and is herein incorporated by reference in its entirety.

"USDA descriptors" are plant variety descriptors described for spinach in the "Objective Description of Variety Spinach (*Spinacia oleracea* L.)—Exhibit C" of the U.S. Department of Agriculture, Agricultural Marketing Service, Science and Technology, Plant Variety Protection Office, Beltsville, Md. 20705, which can be downloaded from the worldwide web at ams.usda.gov/AMSv1.0/ams.fetch Templatepata.do?template=TemplateJ&page=PVPOForms and is herein incorporated by reference in its entirety.

As used herein, the term "plant" includes the whole plant or any parts or derivatives thereof, preferably having the same genetic makeup as the plant from which it is obtained, such as plant organs (e.g., harvested or non-harvested leaves), plant cells, plant protoplasts, plant cell and/or tissue cultures from which whole plants can be regenerated, plant calli, plant cell clumps, plant transplants, seedlings, plant cells that are intact in plants, plant clones or micropropagations, or parts of plants (e.g., harvested cells, tissues or organs), such as plant cuttings, vegetative propagations, embryos, pollen, ovules, fruits, flowers, leaves, seeds, clonally propagated plants, roots, stems, root tips, parts of any of these and the like. Also any developmental stage is included, such as seedlings, cuttings prior or after rooting, mature plants or leaves.

"Harvested plant material" refers herein to plant parts, especially leaves, which have been collected for further storage and/or further use.

"Harvested seeds" refers to seeds harvested from a line or variety, e.g., produced after self-fertilization or cross-fertilization and collected.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) is a variety (i.e., shall be deemed to be essentially derived from another variety, "the initial variety") when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcros sing, or transformation by genetic engineering.

The differences, which result from the act of derivation, may be in one or a few (e.g. two or three) characteristics.

A variant individual from plants of the initial variety may, for example, be selected by sowing seeds of the initial variety and selecting an individual plant which differs in one, two, three, or more morphological or physiological characteristics from the mean of that characteristic (as provided in Table 3). For example, if the initial variety has on average medium-large leaf blades, an individual may be selected which has large leaf blades. Such a variant individual and progeny thereof is an EDV and is encompassed herein.

"Plant line" is for example a breeding line which can be used to develop one or more varieties.

"Hybrid variety" or "F1 hybrid" refers to the seeds harvested from crossing two inbred parental lines. For example, the female parent is pollinated with pollen of the male parent to produce hybrid (F1) seeds.

"Average" refers herein to the arithmetic mean.

DETAILED DESCRIPTION

Spinach is a long-day, flowering plant of the family Amaranthaceae, originating in Asia, but also grown in many temperate regions. It is most productive in cool climates as warm temperatures trigger bolting (flower stalk and seed production). The vegetative, rosette stage produces the marketable leaves, whereas the plant is no longer marketable at the bolting stage, when the flower stalk is formed.

Spinach varieties can differ considerably in earliness. This variation in earliness is desirable to grow varieties under a wide range of growth conditions. The earliness of a variety is determined by its bolting behavior, because the time of bolting determines how early the harvest needs to be. Thus, the earlier a variety bolts, the earlier it is harvested. Earliness or start of bolting (days from sowing until 10% of the plants are flowering) is complex and depends on photoperiod (day length), growth rate and a balance between growth and development. When the photoperiod becomes longer, the rate of bolting increases. The rate of bolting depends on the photoperiod when this ranges from 9 to 20 hours, which covers the day length conditions of the growing areas of spinach (see Parlevliet, 1968, Euphytica 17: 21-27).

Plants grow well in a range of soils, such as sandy loams which are rich in organic matter. Soil pH should not be too acidic, preferably at least a pH of 6 or higher (optimum is about pH 6.2 to 6.9). Moisture supply is important for spinach cultivation as the roots are shallow. Generally fields are irrigated by flooding, furrows or sprinklers.

Varieties are generally classified by their sowing time (spring, summer or winter varieties) and harvesting method (machine or hand). Although spinach is traditionally dioecious (having separate male and female plants), also monoecious types exist with varying degrees of male and female flowers on the same plant (see Pandey, S. C., Kalloo, G. Spinach, *Spinacia oleracea* L. In "Genetic Improvement of Vegetable Crops", (ed. G. Kalloo, B. O. Bergh), Pergamon Press, Oxford, U.K., pp. 325-336 (1993)).

A number of characteristics are important to spinach breeders including (but not limited to) disease resistance, earliness/start of bolting (early, medium or late), growth habit and leaf characteristics.

The present invention provides a new hybrid variety, NUN 0002 SP, which is a smooth/flat leaf type with smooth seeds and with arrow-shaped, medium green, dull leaves at market stage, which have a round-pointed tip, a lobed base and a slightly curled margin. Andromeda has a medium-to-late earliness (start of bolting is medium to late), and is about 2 or 3 days earlier than Whale and about 1 or 2 days earlier than Lazio. Also the harvest date is about 2 or 3 days earlier than Whale and about 1 or 2 days earlier than Lazio. Andromeda has a medium growth rate, similar to Lazio. Petioles have a medium length, different from Lazio (with a short petiole length). Plant habit of Andromeda at prime market stage is semi-erect, while that of Lazio is flat. Leaf blistering is medium (comparable to Butterblay, Koala, Mystic). NUN 0002 SP has high seedling and field resistance against downy mildew races Pf 1-11 and UA2209.

TABLE 1

Seedling resistance, as described in Correll et al, 2010 (Guidelines for Spinach Downy Mildew, last updated 29 Oct. 2010, from the worldwide web at worldseed.org/cms/medias/file/TradeIssues/ DiseasesResistance/Differentials/)

| Race of *Peronospora farinose* f.sp. *spinaciae* | Lazio | Whale | Andromeda |
|---|---|---|---|
| 1 | R | R | R |
| 2 | R | R | R |
| 3 | R | R | R |
| 4 | R | IR | R |

TABLE 1-continued

Seedling resistance, as described in Correll et al, 2010
(Guidelines for Spinach Downy Mildew, last
updated 29 Oct. 2010, from the worldwide web at
worldseed.org/cms/medias/file/TradeIssues/
DiseasesResistance/Differentials/)

| Race of Peronospora farinose f.sp. spinaciae | Lazio | Whale | Andromeda |
|---|---|---|---|
| 5 | R | R | R |
| 6 | R | IR | R |
| 7 | R | IR | R |
| 8 | R | R | R |
| 9 | R | R | R |
| 10 | R | S | R |
| 11 | S | R | R |
| UA 2209 | S | S | R |
| 510C | S | Not tested | Not tested |

R = high resistance (no sporulation observed on cotyledons)
IR = intermediate resistance (sparse sporulation on the tips of cotyledons)
S = susceptible (sporulation on cotyledons)

The morphological and/or physiological characteristics may vary with variation in the environment (such as temperature, light intensity, day length, humidity, soil, fertilizer use), which is why a comparison under the same environmental conditions is preferred. Colors can best be measured against the Royal Horticultural Society Chart (on the worldwide web at rhs.org.uk/Plants/RHS-Publications/RHS-colour-charts). Thus, comparisons to other varieties is preferably done by growing Andromeda and comparison varieties in one or two independent growing cycles under the same growing and environmental conditions. Morphological and physiological characteristics are determined on at least 10, preferably at least 15, more preferably at least 20 individual plants, in order to determine the average for the characteristic.

Andromeda can be grown in spring, winter or fall. It can also be used for baby leaf production. In the USA 90% of spinach is grown in California and Arizona. In the Salinas Valley plantings begin mid February and continue until mid October. It takes between about 21 and 47 days from seeding to maturity and harvest. In the Imperial Valley and Yuma Valley planting is during late fall and winter. It takes between about 21 to 55 days from seeding to harvest.

The leaves of Andromeda can be harvested for fresh, canned or frozen use. Harvested leaves can be loose or in bunches or pillow-packed, washed and packaged, e.g. in bags, cellophane, optionally in air or nitrogen gas to extend shelf-life. Harvested leaves are washed, rinsed and slightly dried before packaging or further processing. Harvested leaves can for example be chopped or cut, frozen, steamed, etc. Packages can, thus, comprise fresh spinach leaves or processed spinach, such as frozen spinach. Canned spinach is also commonly produced. In one aspect harvested and/or packaged and/or processed leaves of Andromeda are provided herein. Harvest of spinach leaves may be by machine harvest or by hand. For fresh-leaf packaging it is important that the leaves are kept cool after harvest, during packaging and transport in order to ensure fresh and attractive products with a good shelf-life.

Seeds of spinach variety NUN 0002 SP are provided herein, wherein a representative sample of said seeds (2500 seeds) is to be deposited, under the Budapest Treaty, under Accession Number NCIMB 42156.

Seeds of NUN 0002 SP are obtainable by crossing the male inbred parent with the female inbred parent and harvesting the seeds produced. The resultant NUN 0002 SP seeds can be grown to produce NUN 0002 SP plants. In one embodiment a plurality of NUN 0002 SP seeds are packaged into small and/or large containers (e.g., bags, cartons, cans, etc.). The seeds may be treated with various compounds, such as seed coatings and/or pelleting compounds. Seed treatment may include fungicide, herbicide and/or insecticide coatings, and/or biological control agents. Benomyl (Benlate) is for example used as seed treatment for controlling early stages of Fusarium wilt, caused by *Fusarium oxysporum* f.sp. *spinaciae*. Other chemical agents which may be used as seed treatments are listed further below.

Also provided are plants of spinach variety NUN 0002 SP, or a part thereof, produced from seeds, wherein a representative sample of said seeds is to be deposited under Accession Number NCIMB 42156. Plants of NUN 0002 SP can be produced by seeding directly in the ground (e.g. field). A method for growing Andromeda plants is also encompassed herein, comprising seeding of Andromeda seeds in the ground and allowing the plants to grow to maturity. The field may be irrigated to ensure appropriate moisture and/or chemical agents may be applied one or more times for weed, disease and pest control.

Herbicides include the following: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam. Insecticides include the following: Aldicarb, Bacillus thuriengiensis, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid. Funicides include the following: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin.

Weeds are commonly controlled by applying e.g. Phenmedipham, Cycloate, Ethofumesate, Fluazifop-P-butyl, S-Metolachlor and/or Diquat. Downy mildew can be controlled by e.g. Cymoxanil, Mefenoxam, Chlorothalonil, Copper hydroxide, Copper oxychloride and basic copper sufate, Fosetyl-aluminum and/or Azoxystrobin. Leaf spot complex (*Cladosporium* variable, *Stemphylium botryosum* and others) can be controlled by e.g. Chlorothalonil, Mancozeb, Azoxystrobin, and/or Pyraclostrobin. *Pythium* and *Rhizoctonia* spp can e.g. be controlled by Metalaxyl and/or Mefenoxam. Aphids may be controlled by e.g. Pymetrozine. Cutworms, armyworms and loopers may be controlled by e.g. Dimethoate or Permethrin. European Cranfly (*Tipula palu-*

*dosa*) may for example be controlled by Carbofuran. Springtail (*Onychuirus pseudarmatus*) may e.g. be controlled by Carbofuran.

Parts of NUN 0002 SP encompass any cells, tissues, organs obtainable from the seedlings or plants, such as but not limited to: leaves, cuttings, pollen and the like. Such parts (especially leaves) can be stored and/or processed further. Encompassed are therefore also food or feed products comprising one or more of such parts, such as fresh, frozen or canned leaves obtainable from NUN 0002 SP or from progeny thereof, or from a derived variety or variant, such as an EDV.

In a preferred embodiment, the invention provides for leaves of spinach variety NUN 0002 SP, or a part of the leaves. The leaves are preferably mature leaves or baby leaves. They may be harvested and stored and/or processed further. In another embodiment, the invention provides for a container comprising or consisting of a plurality of harvested leaves of NUN 0002 SP, or progeny thereof, or a variant or derived variety, such as an EDV.

In yet a further embodiment, the invention provides for a method of producing a new spinach plant, such as a line or variety. The method comprises crossing NUN 0002 SP, either as male or as female parent, with a second spinach plant one or more times, and/or selfing NUN 0002 SP one or more times, and selecting progeny from said crossing and/or selfing. The second plant may be a line or variety of any type, i.e. savoy (wrinkled leaf), semi-savoy (semi-wrinkled) or flat-leaf spinach. The second plant may also be a landrace or wild species, e.g. a line found in genebank collections, such as *S. turkestanica, S. tetranda*, or others. Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another spinach plant. Using common breeding methods such as backcrossing or recurrent selection, mass selection or progeny testing, one or more specific characteristics may be introduced into NUN 0002 SP, to provide an EDV of NUN 0002 SP. Also a variant of the initial variety may be produced in this way, which differs in one, two, three or more characteristics, e.g. of those of Table 2 and/or 3, from the initial variety.

The invention provides for methods of producing varieties which retain all the morphological and physiological characteristics of NUN 0002 SP, or EDVs (Essentially Derived Varieties), which may differ from NUN 0002 SP in one, two, three or more morphological and/or physiological characteristics, but which are still genetically closely related to NUN 0002 SP. The relatedness can, for example be determined by fingerprinting techniques (e.g. making use of isozyme markers and/or molecular markers such as SNP markers (Single Nucleotide Polymorphisms), AFLP markers, microsatellites, minisatellites, RAPD markers, RFLP markers, SCAR markers, and others, such as TRAP markers described by Hu et al. 2007, Genet Resour Crop Evol 54: 1667-1674). A plant is "closely related" to NUN 0002 SP (and thus being an EDV) if its DNA fingerprint is at least 80%, 85%, 90%, 95%, 96%, 97% or 98% identical to the fingerprint of NUN 0002 SP. In a preferred embodiment AFLP markers are used for DNA fingerprinting (Vos et al. 1995, Nucleic Acid Research 23: 4407-4414 and EP534858). Alternatively, a closely related plant may have a DICE coefficient of similarity of at least 0.80, 0.85, 0.86, 0.87, 0.88, 0.89, 0.9 or higher (see Hu et al., 2007, supra).

By crossing and/or selfing also (one or more) single traits may be introduced into NUN 0002 SP (e.g. using backcrossing breeding schemes), while retaining the remaining morphological and physiological characteristics of NUN 0002 SP. For example, disease resistance genes may be introduced, genes responsible for one or more quality traits (e.g. higher carotenoid content, higher iron content, lower nitrate content, lower oxalic acid content), yield, cold resistance, delayed bolting, etc. Both single genes (dominant or recessive) and one or more QTLs (quantitative trait loci) may be transferred into NUN 0002 SP by breeding with NUN 0002 SP. Inheritance of prickly versus smooth seeds, smooth versus savoy leaves, light green versus dark green leaves and short versus long petiole are mostly monogenic, while winter hardiness, growth rate, and yield are genetically more complex (see Pandey and Kalloo 1993, supra).

Any pest and/or disease resistance genes may be introduced into NUN 0002 SP, progeny thereof or into an EDV of NUN 0002 SP. Resistance to one or more of the following diseases is preferably present and/or introduced into plants of the invention: *Peronospora farinose* f.sp. *spinaciae* resistance genes, e.g. to new races and/or race 510C; white rust (*Albugo occidentalis*) resistance genes, *Fusarium oxysporum* f.sp. *spinaciae* resistance genes, *Pythium* resistance, *Rhizoctonia* resistance, *Colletotrichum anthracnose* resistance, *Cercospora beticola* resistance, *Verticillium dahliae* resistance, *Phytophthora* ssp, *Stemphylium* leaf spot resistance, Curly Top Virus resistance, Cucumber Mosaic Virus (CMV) resistance, Impatiens Necrotic Spot Virus (INSV), Beet Yellows and/or Beet mosaic resistance, leaf miner resistance, and others. PI 169685 and PI 173809 for example comprise resistance against Stemphylium, which can be introduced into Andromeda by breeding methods.

Thus, the invention also provides a method for developing a spinach plant in a spinach breeding program, using a spinach plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 0002 SP or progeny thereof with a different spinach plant, and wherein one or more offspring of the cross are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

Encompassed herein is, in one aspect, a method of introducing a desired trait into NUN 0002 SP comprising:
  (a) crossing a plant of variety NUN 0002 SP, a representative sample of seed of said variety to be deposited under Accession Number NCIMB 42156, with a second spinach plant comprising a desired trait to produce F1 progeny plants;
  (b) selecting F1 progeny plants that comprise the desired trait to produce selected F1 progeny plants;
  (c) crossing the selected F1 progeny plants with at least a first plant of NUN 0002 SP to produce backcross progeny plants;
  (d) selecting backcross progeny plants comprising the desired trait and the physiological and morphological characteristics of NUN 0002 SP to produce selected backcross progeny plants; and
  (e) repeating steps (c) and (d) one or more times in succession to produce selected second or higher backcross progeny plants that comprise the desired trait and otherwise comprise all of the physiological and morphological characteristics of NUN 0002 SP when grown in the same environmental conditions.

Provided is also a spinach plant produced by the above method.

In one aspect a spinach plant comprising all the morphological and physiological characteristics of NUN 0002 SP as depicted in Table 2 and/or 3 is provided, but wherein said spinach plant differs in one, two or three of the characteristics, and wherein the combination of the morphological and physiological characteristics which are the same as in NUN 0002 SP are controlled by genetic means found in spinach variety NUN 0002 SP, a representative sample of seed of said variety to be deposited under Accession Number NCIMB 42156.

Also provided herein is a spinach plant that exhibits a combination of traits of at least 2, 3, 4, 5, 6, 7 or more of those of variety NUN 0002 SP of Table 2 and/or 3.

In particular, a plant is provided comprising at least 2, 3, 4, 5 or more morphological and physiological characteristics selected from the group consisting of: arrow-shaped leaves (market stage), medium green upper leaf color, dull leaf luster, medium-to-late start of bolting (earliness), spineless seeds (smooth seed surface), semi-erect plant habit, resistance to downy mildew (*Peronospora farinose* f.sp. *spinaciae*) races Pf 1-11 and race UA2209, wherein the combination of traits is controlled by genetic means found in spinach variety NUN 0002 SP, a representative sample of seed of said variety to be deposited under Accession Number NCIMB 42156.

In a further embodiment a plant is provided comprising at least 2, 3, 4, 5 or more morphological and physiological characteristics selected from the group consisting of: medium growth rate, semi-erect plant habit, a smooth seed surface, a flat margin of the first foliage leaves, a round-pointed tip of the prime market stage leaves, lobed blades, medium petiole length (at least about 10, 11, 12 or 13 cm on average), no red pigmentation of the petioles and resistance to downy mildew (*Peronospora farinose* f.sp. *spinaciae*) races Pf 1-11 and race UA2209, wherein the combination of traits is controlled by genetic means found in spinach variety NUN 0002 SP, a representative sample of seed of said variety to be deposited under Accession Number NCIMB 42156.

In one embodiment natural variants of NUN 0002 SP may be selected, which differ from NUN 0002 SP in at least 1, 2, 3 or more morphological and physiological traits as described herein.

In one embodiment, NUN 0002 SP may also be mutated (by e.g. irradiation, chemical mutagenesis, heat treatment, etc.) and mutated seeds or plants may be selected in order to change one or more characteristics of NUN 0002 SP. Also natural mutants may be identified and used in breeding. Methods such as TILLING and/or EcoTILLING may be applied to spinach populations in order to identify mutants. Similarly, NUN 0002 SP may be transformed and regenerated, whereby one or more chimeric genes are introduced into the variety. Transformation and regeneration can be carried out using standard methods, such as *Agrobacterium tumefaciens* mediated transformation or biolistics, followed by selection of the transformed cells and regeneration into plants. See e.g. Al-Khayri, 1995, Biotech in Agricult and Forestry Vol. 34, pp 279-288 or Knoll et al. 1997, Plant Cell Reports 17: 96-101). A desired trait (e.g. genes conferring pest or disease resistance, herbicide, fungicide or insecticide tolerance, etc.) can be introduced into NUN 0002 SP, or progeny thereof, by transforming NUN 0002 SP or progeny thereof with a transgene that confers the desired trait, wherein the transformed plant retains all the morphological and physiological characteristics of NUN 0002 SP or the progeny thereof and contains the desired trait.

The invention also provides for progeny of spinach variety NUN 0002 SP obtained by further breeding with NUN 0002 SP. In one aspect progeny are F1 progeny obtained by crossing NUN 0002 SP with another plant or S1 progeny obtained by selfing NUN 0002 SP. Thus, plants obtained by using NUN 0002 SP as male or female parent are provided herein and a method of using NUN 0002 SP as a male or female parent. Also encompassed are F2 progeny obtained by selfing the F1 plants (obtained from self pollinating or cross pollinating NUN 0002 SP). "Further breeding" encompasses traditional breeding (e.g., selfing, crossing, backcrossing), marker assisted breeding, and/or mutation breeding. In one embodiment, the progeny have all the physiological and morphological characteristics of variety NUN 0002 SP when grown under the same environmental conditions. In another embodiment the progeny are EDVs and/or have one, two, or three distinct traits (qualitative or quantitative) introduced into NUN 0002 SP, while retaining all the other physiological and morphological characteristics of variety NUN 0002 SP when grown under the same environmental conditions.

The variety NUN 0002 SP or a variant thereof (e.g. an EDV), or its progeny, can also be reproduced using vegetative reproduction methods. Therefore, the invention provides for a method of producing plants, or a part thereof, of variety NUN 0002 SP comprising vegetative propagation of variety NUN 0002 SP. Vegetative propagation comprises regenerating a whole plant (e.g. a seedling) from a part of variety NUN 0002 SP or of a variant thereof, such as a cutting, a cell culture, protoplast culture or a tissue culture (e.g., in vitro leaf disks, hypocotyl segments, root segments, etc.). The term "cell culture" encompasses a protoplast culture herein. The method comprises establishing a cell culture or tissue culture of NUN 0002 SP or a variant thereof (comprising regenerable cells), or progeny thereof or an EDV thereof, and at an appropriate time, e.g. after callus formation, transferring the culture to a shoot induction medium to allow shoot regeneration and to a root induction medium to allow root development. A whole plant is regenerated, which has the genetic makeup of the initial plant. Such vegetative propagations of NUN 0002 SP (or of progeny or an EDV thereof) have all the morphological and physiological characteristics of NUN 0002 SP (or of the progeny or the EDV) and are an embodiment of the invention, as are any parts thereof.

The invention also provides for a vegetatively propagated plant of variety NUN 0002 SP, or a part thereof, having all the morphological and physiological characteristics of NUN 0002 SP when grown under the same environmental conditions.

In one aspect, the invention encompasses a cell-, tissue-, or protoplast culture comprising regenerable cells of NUN 0002 SP, or progeny thereof or an EDV thereof. Any plant part may be used to establish such a culture, e.g. pollen, microspores, embryos, leaves or parts thereof, hypocotyls or parts thereof, seeds or parts thereof, flowers or parts thereof, etc.

In one aspects haploid plants and/or double haploid (DH) plants of NUN 0002 SP are encompassed herein, as are polyploids, such as tetraploids. Haploid and double haploid (DH) plants can for example be produced by anther or microspore culture and regeneration into a whole plant. For DH production or polyploidy (e.g. tetraploid) production chromosome doubling may be induced using known methods, such as colchicine treatment or the like.

Also provided are plant parts derived from variety NUN 0002 SP, or from a vegetatively propagated plant of NUN 0002 SP, being selected from the group consisting of: leaves or parts thereof, pollen, cells, petioles, shoots or parts thereof, stems or parts thereof, roots or parts thereof, cuttings, protoplasts, flowers or parts thereof, flower buds, flower stalks or parts thereof, seeds or parts thereof, embryos, etc.

The invention also provides for a food or feed product comprising or consisting of a plant part described herein. The food or feed product may be fresh and/or processed, e.g., canned, steamed, boiled, fried, blanched and/or frozen, etc.

For example, containers such as cans, boxes, crates, bags, cartons, Modified Atmosphere Packagings, films (e.g. biodegradable films), etc. comprising plant parts of the spinach varieties (fresh and/or processed) described herein are also provided herein.

All documents are herein incorporated by reference in their entirety.

EXAMPLES

Development of NUN 0002 SP

The hybrid NUN 0002 SP was developed by crossing a proprietary female and male inbred parent line. The inbred parental lines were developed through several generations of recurrent selection and inbreeding.

The seeds of NUN 0002 SP can be grown to produce hybrid plants and parts thereof (e.g. leaves). The hybrid variety NUN 0002 SP can be propagated by seeds or vegetative.

The hybrid variety NUN 0002 SP is uniform and genetically stable. This has been established through evaluation of horticultural characteristics.

A total of 2500 seeds of the hybrid variety NUN 0002 SP (also called "Andromeda" or "Andromeda F1") were deposited by Nunhems B. V. on Aug. 15, 2013, at the NCIMB Ltd., Ferguson Building, Craibstone Estate, Bucksburn, Aberdeen AB21 9YA, United Kingdom (NCIMB). The deposit has been assigned Accession Number NCIMB 42156. A deposit of NUN 0002 SP and of the male and female parent line is also maintained at Nunhems B. V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Characteristics of NUN 0002 SP

Table 2 shows morphological and physiological distinguishing characteristics of NUN 0002 SP compared to the most similar varieties, Lazio and Whale.

TABLE 2

| Morphological and Physiological Characteristic | Lazio | Whale | NUN 0002 SP (Andromeda) |
|---|---|---|---|
| Earliness/start of bolting | 1 June | 2 June | 30 May (=2 or 3 days earlier than Lazio or Whale, respectively) |

TABLE 2-continued

| Morphological and Physiological Characteristic | Lazio | Whale | NUN 0002 SP (Andromeda) |
|---|---|---|---|
| Pf resistance | Pf 1-10 | Pf 1-9, 11 | Pf 1-11, US2209 |
| Plant habit (prime market stage) | Flat | n.d. | Semi-erect |
| Margin (First foliage leaf) | Slightly curled | n.d. | Flat |
| Tip (Prime market stage leaf) | Round | n.d. | Round-pointed |
| Lobing (Prime market stage leaf) | Not lobed | n.d. | Lobed |
| petiole: red pigmentation (Prime market stage leaf) | present | n.d. | Absent | n.d. = not determined

Andromeda has not only an earlier bolting date than Lazio and Whale, but also an earlier harvest date, which is about 2 days earlier than Lazio and 3 days earlier than Whale. Lazio has a bolting and harvest date of about 1 day earlier than Whale.

Table 3 shows the physiological and morphological characteristics of commercial varieties Lazio compared to the hybrid variety Andromeda. The data are based on a trial in the Netherlands in 2010, carried out on behalf of Nunhems B. V. by the Nak-tuinbouw, Roelofarendsveen, The Netherlands. USDA descriptors were used in the trial evaluation. Measurements are based on at least 15 to 25 randomly selected plants or plant parts and average values are provided.

TABLE 3

| USDA descriptor (Exhibit C) | Andromeda F1 | Lazio |
|---|---|---|
| Species | *Spinacia oleracea* L. | *Spinacia oleracea* L. |
| ploidy | diploid | diploid |
| Maturity | | |
| Growth Rate | medium | medium |
| Slow - Norgreen; Medium - Long Standing Bloomsdale | | |
| Days from planting to prime market stage | 36 | 36 |
| PLANT (prime market stage) | | |
| Habit | Semi-erect | flat |
| Flat - Viroflay; semi-erect - Long Standing Bloomsdale | | |
| Size | medium | medium |
| Spread (cm) | 45 | 40 |
| Height (cm) | 15 | 13 |
| SEEDLING COTYLEDON | | |
| Width (mm) | 7-8 | 8 |
| Length (mm) | 90-100 | 80 |
| Tip | Rounded, but a little pointed | Rounded, but a little pointed |
| Color | Medium green | Medium green |
| Color chart (RHS) | 146B | 146B |
| LEAF (first foliage leaves) | | |
| Shape | elliptic | elliptic |
| Base | V-shaped | V-shaped |
| Tip | pointed | pointed |
| margin | flat | Slightly curled |

TABLE 3-continued

| USDA descriptor (Exhibit C) | Andromeda F1 | Lazio |
|---|---|---|
| Upper surface color (Medium green - Giant Nobel) | Medium green | Medium green |
| Color chart (RHS) | 146A | 146A |
| Lower surface color (compared to upper surface color) | lighter | lighter |
| Color chart (RHS) | Between 146A and 146B | 146B |
| LEAF (prime market stage) | | |
| Surface (smooth - Viroflay) | smooth | smooth |
| shape | Arrow-shaped | Arrow-shaped |
| base | lobed | lobed |
| tip | Round-pointed | round |
| margin | Slightly curled | Slightly curled |
| Upper surface color | Medium green (Giant Nobel) | Medium green (Giant Nobel) |
| Color chart name (RHS) | 146A | 146A |
| Lower surface color (compared with upper surface) | lighter | lighter |
| Color chart name (RHS) | 146B | 146B |
| luster | dull | dull |
| Blade size (medium - Virginia Savoy; Large - Giant Nobel) | Medium-large | Medium |
| Blade lobing | lobed | Not lobed |
| Petiole color | Medium green | Medium green |
| Color chart name (RHS) | 146B | 144A |
| Petiole red pigmentation | absent | present |
| Petiole length to the blade (cm) | 13 | 9 |
| Petiole length | medium | short |
| Petiole diameter (mm) | 9 | 8 |
| Petiole diameter | medium | medium |
| SEED STALK DEVELOPMENT | | |
| Start of bolting (10% of plants) Early = Dixie Market Medium = Long Standing Bloomsdale Late = Norgreen | Earlier than late (medium-to-late) | Late |
| Height of stalk (cm) | 85 | 85 |
| Leaves on stalk of female plant | many | many |
| Leaves on stalk of male plant | — | — |
| Plants that are female | 0-10% | 0-10% |
| Plants that are male | 0-10% | 0-10% |
| Plants that are monocious | 91-100% | 91-100% |
| SEED | | |
| Surface | smooth | smooth |
| Downy Mildew (Pf) race 1 | Resistant | Resistant |
| Downy Mildew (Pf) race 2 | Resistant | Resistant |
| Downy Mildew (Pf) race 3 | Resistant | Resistant |
| Fusarium wilt | Not tested | Not tested |
| White rust | Not tested | Not tested |
| Curly Top Virus | Not tested | Not tested |
| Cucumber Mosaic Virus | Not tested | Not tested |
| Downy Mildew Races 4-11 | resistant | Susceptible to Pf 11 |
| Downy Mildew Race UA 2209 | resistant | susceptible |

These are typical values.
Values may vary due to environment.
Other values that are substantially equivalent are also within the scope of the invention.
RHS = Royal Hortic. Soc. Color Chart

The invention claimed is:

1. Seed of spinach variety NUN 0002 SP, wherein a representative sample of said seed has been deposited under Accession Number NCIMB 42156.

2. A plant grown from the seed of claim 1.

3. A plant part of the plant of claim 2, wherein said part is selected from the group consisting of leaves or parts thereof, cells, petioles, shoots or parts thereof, stems or parts thereof, roots or parts thereof, cuttings, protoplasts, flowers or parts thereof, flower buds, flower stalks or parts thereof, and cotyledons.

4. A spinach plant having all the morphological and physiological characteristics of the spinach plant of claim 2.

5. A tissue or cell culture of regenerable cells of spinach variety NUN 0002 SP, wherein a representative sample of said seed has been deposited under Accession Number NCIMB 42156.

6. The tissue or cell culture according to claim 5, comprising cells or protoplasts from a plant part selected from the group consisting of leaves, embryos, meristems, cotyledons, petioles, hypocotyl, pollen, microspores, anthers, roots, root tips, stalks, seeds, shoots, flowers and pistils.

7. A spinach plant regenerated from the tissue or cell culture according to claim 6, wherein the regenerated plant expresses all the morphological and physiological characteristics of NUN 0002 SP, wherein a representative sample of said seed has been deposited under Accession Number NCIMB 42156.

8. A method of producing a spinach plant or spinach seed, comprising crossing the plant of claim 2 with a second spinach plant one or more times, and selecting progeny from said cross.

9. A method of producing a spinach plant or spinach seed, comprising selfing the plant of claim 2 one or more times, and selecting progeny from said selfing.

10. Progeny of spinach variety NUN 0002 SP obtained by further breeding with said variety, wherein a representative sample of seed of NUN 0002 SP has been deposited under Accession Number NCIMB 42156, and wherein said progeny have all the physiological and morphological characteristics of variety NUN 0002 SP when grown under the same environmental conditions.

11. A method of producing plants, or a part thereof, of variety NUN 0002 SP, wherein a representative sample of seed of variety NUN 0002 SP has been deposited under Accession Number NCIMB 42156, comprising vegetative propagation of variety NUN 0002 SP.

12. The method of claim 11, wherein said vegetative propagation comprises regenerating a whole plant from a part of variety NUN 0002 SP.

13. A vegetative propagated plant of variety NUN 0002 SP, wherein a representative sample of seed of variety NUN 0002 SP has been deposited under Accession Number NCIMB 42156, or a part thereof, having all the morphological and physiological characteristics of NUN 0002 SP when grown under the same environmental conditions.

14. Plant parts derived from variety NUN 0002 SP, wherein a representative sample of seed of variety NUN 0002 SP has been deposited under Accession Number NCIMB 42156, or from a plant of claim 13, wherein said plant part are harvested leaves or parts thereof, cells, flowers or parts thereof, petioles, hypocotyls, shoots or parts thereof, stems or parts thereof, roots or parts thereof, cuttings, stalks or parts thereof, or flower buds.

15. A container comprising a plant part of claim 14.

16. The container of claim 15, wherein said plant part is fresh or processed spinach leaves.

17. A method of producing a spinach plant having a desired trait, wherein the method comprises transforming the spinach plant of claim 2 with a transgene that confers the desired trait, wherein the transformed plant retains all the phenotypic and morphological characteristics of variety NUN 0002 SP and contains the desired trait, a representative sample of seed of said variety NUN 0002 SP having been deposited under Accession Number NCIMB 42156.

18. A spinach plant produced by the methods of claim 17, wherein the plant comprises the desired trait and all of the physiological and morphological characteristics of NUN 0002 SP.

19. A method of introducing a desired trait into NUN 0002 SP comprising:
   (a) crossing a plant of variety NUN 0002 SP, a representative sample of seed of said variety having been deposited under Accession Number NCIMB 42156, with a second spinach plant comprising a desired trait to produce F1 progeny plants;
   (b) selecting F1 progeny plants that comprise the desired trait to produce selected F1 progeny plants;
   (c) crossing the selected F1 progeny plants with at least a first plant of NUN 0002 SP to produce backcross progeny plants;
   (d) selecting backcross progeny plants comprising the desired trait and the physiological and morphological characteristics of NUN 0002 SP to produce selected backcross progeny plants; and
   (e) repeating steps (c) and (d) one or more times in succession to produce selected second or higher backcross progeny plants that comprise the desired trait and otherwise comprise all of the physiological and morphological characteristics of NUN 0002 SP when grown in the same environmental conditions.

20. A spinach plant produced by the method of claim 19.

* * * * *